United States Patent [19]

Columbus

[11] Patent Number: 5,007,892
[45] Date of Patent: Apr. 16, 1991

[54] PHASE SEPARATION CONTAINER WITH FIXED MEANS PREVENTING REMIXING

[75] Inventor: Richard L. Columbus, Rochester, N.Y.

[73] Assignee: Eastman Kodak Company, Rochester, N.J.

[21] Appl. No.: 325,725

[22] Filed: Mar. 20, 1989

[51] Int. Cl.⁵ .............................................. B04B 11/04
[52] U.S. Cl. ..................................... 494/17; 210/515; 210/516
[58] Field of Search .................... 494/16, 17; 210/516, 210/521, 523, 538, 522; 128/637

[56] References Cited

U.S. PATENT DOCUMENTS

| 3,908,893 | 9/1975 | Williams | 494/17 X |
| 4,012,325 | 3/1977 | Columbus . | |
| 4,169,060 | 9/1979 | Columbus . | |
| 4,202,778 | 5/1980 | Middelbeck | 210/522 |
| 4,343,709 | 8/1982 | Okumura | 494/17 X |
| 4,402,680 | 9/1983 | Schoendorfer | 494/17 X |

Primary Examiner—Daniel M. Yasich
Attorney, Agent, or Firm—Dana M. Schmidt

[57] ABSTRACT

There is described a container for phase separation of at least two phases via centrifugation. Means are provided to prevent remixing, such means comprising porous mechanical means such as surfaces fixed in place and inclined at an angle to resist flow of the heavier phase upon removal of the lighter phase, such that remixing of the phases is prevented.

9 Claims, 3 Drawing Sheets

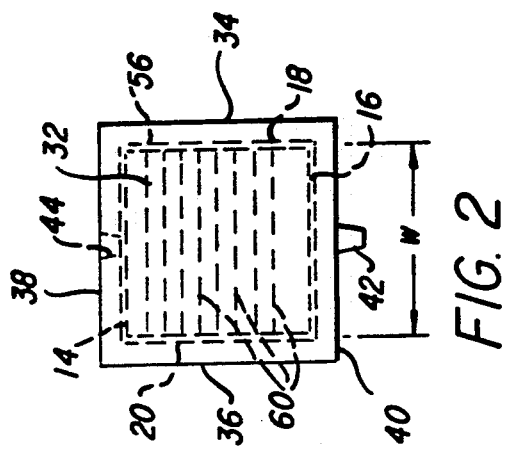
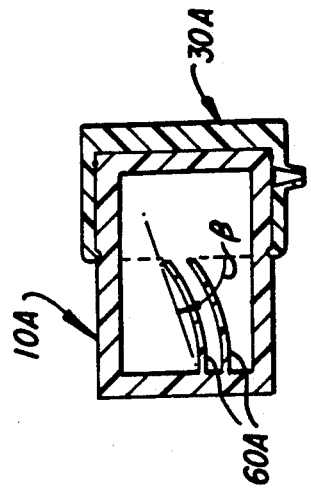
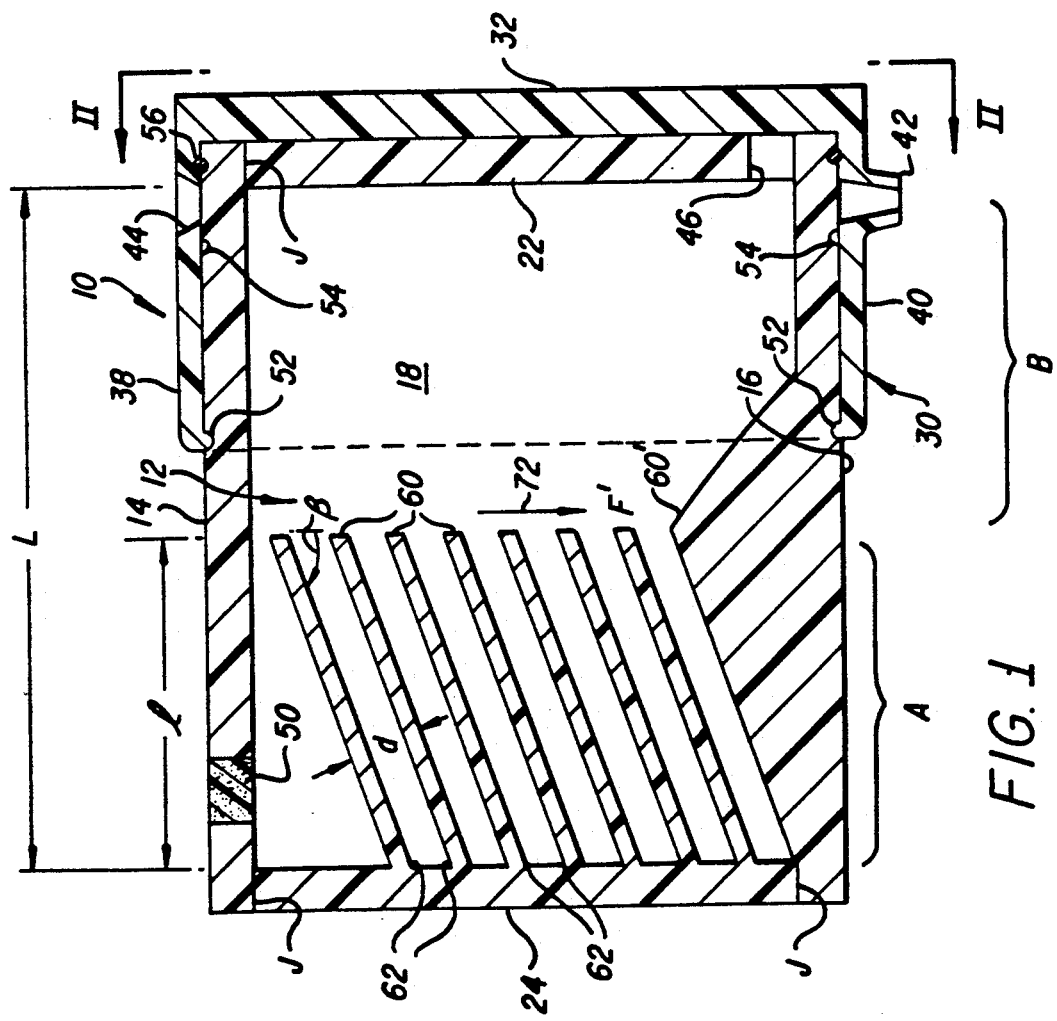

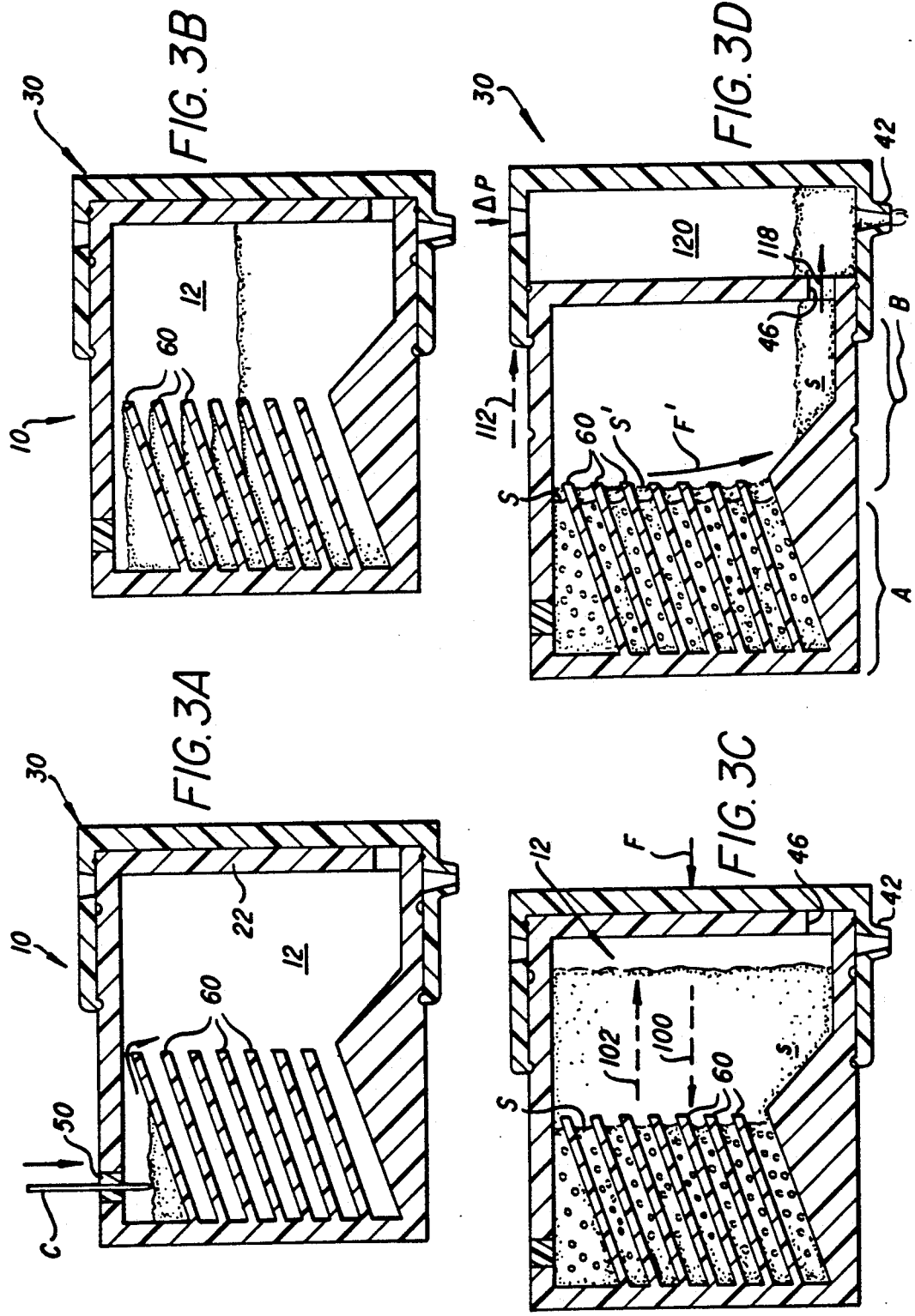

PHASE SEPARATION CONTAINER WITH FIXED MEANS PREVENTING REMIXING

FIELD OF THE INVENTION

This invention relates to containers for separating a light phase from a heavy phase of a liquid and for allowing the separated light phase to be dispensed without remixing the heavier phase.

BACKGROUND OF THE INVENTION

Blood collection and phase separation containers are known in the art, for collecting whole blood and separating the light serum from the heavier cells. Such containers have a compartment for collecting the blood, wherein phase separation occurs during centrifugation, and some kind of maintaining means for maintaining the serum separate from the cells, once centrifuge separation is finished. A valve can also be included to allow the separated serum to flow elsewhere. The maintaining means can be a gel that is formulated or constructed to seek a specific gravity that is in between that of the two phases being separated. Examples of such prior containers are shown in U.S. Pat. No. 4,012,325. Porous mechanical barriers can be used to assist the gel, as shown in U.S. Pat. No. 4,169,060, but these are not effective without the gel, nor are they positioned to work without the gel.

Such containers have been proven to be highly effective. Their only drawback, which has been minor, is the complication created by having to assemble such a device with a gel and/or mechanical barrier that is movable with respect to the compartment. It is desired in such assembly that the gel and/or mechanical barrier be correctly positioned at the start of the operation, to preclude heavier phase material from contacting portions intended to contact only the lighter phase. Thus, more care has been needed in assembly than would be the case if the maintaining means were somehow a fixed feature of the compartment. However, because the ratios of lighter to heavier phase are unpredictable, at least with blood samples, it has been thought impractical to position maintaining means only at one location to satisfy all possible conditions to be encountered. Thus, prior constructions use a movable maintaining means that will seek out its correct position.

Therefore, prior to this invention there has been a need for a phase separation container having fixed maintaining means that will accommodate expected variations in phase volumes, so that the fixed maintaining means can be manufactured automatically while manufacturing the rest of the container.

SUMMARY OF THE INVENTION

I have constructed a fixed mechanical means for maintaining the separation of the heavier and lighter phase in such a container.

More specifically, there is provided a centrifuge container for separating two phases of different specific gravities in a liquid by centrifuging the heavier phase away from the lighter phase, the container including a compartment for the liquid defined by opposing walls, and means in the compartment for maintaining the phases separate after centrifugation. The container is improved in that the means comprise porous mechanical means for resisting flow of the heavier phase out of its compartment portion in the presence of shear forces occurring when the lighter phase is drawn off, the mechanical means being disposed in the compartment region to be occupied by the heavier phase.

In a preferred embodiment, the mechanical means is fixed to the region to be occupied by the heavier phase.

Accordingly, it is an advantageous feature of the invention that there is provided a centrifuge container in which the means for maintaining phase separation is a fixed feature of the container as manufactured.

It is a related advantageous feature of the invention that there is no need to correctly place the means for maintaining phase separation as part of the assembly operation, since it is a fixed, built-in feature of the container.

Other advantageous features will be readily apparent upon reference to the following description of the preferred embodiments when read in light of the attached drawings.

BRIEF DESCRIPTION OF THE DRAWINGS

FIG. 1 is an elevational section view of a container made in accordance with the invention;

FIG. 2 is an end view taken generally along the line II—II of FIG. 1;

FIG. 3A-3D are section views similar to those of FIG. 1, illustrating the use of the container;

FIGS. 4 and 5 are section views similar to that of FIG. 1, illustrating alternate embodiments of the baffle plate.

DESCRIPTION OF THE PREFERRED EMBODIMENTS

Figure 5:
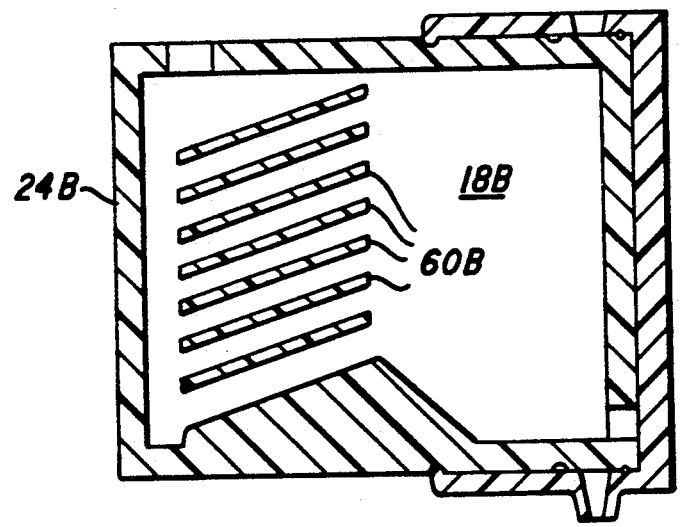

The invention is described in connection with a preferred embodiment wherein it is used to separate blood into serum and blood cells, using a rectangular configuration for the container, that is, one having six outside surfaces perpendicularly disposed to each other. In addition, the invention is applicable regardless of the nature of the liquid separated into its phases, regardless of the number of phases more than one, and regardless of the outside shape of the container. It is further useful when the container of this invention is incorporated into a larger container that provides phase separation as only one of several integrated functions.

Turning first to FIGS. 1 and 2, a container 10 for separating a multi-phase liquid into at least a heavier phase and a lighter phase, and particularly blood cells and blood serum, comprises a compartment 12 comprising three pairs of opposing outside walls 14, 16; 18, 20; and 22, 24. In addition, a telescoping member 30 forms a valve and a serum dispensing chamber. Member 30 comprises a cap formed from end wall 32 and sidewalls 34, 36, 38 and 40. Member 30 has features and functions substantially as described in U.S. Pat. No. 4,091,802, the details of which are expressly incorporated herein by reference. Metering tip 42 is used with an air access aperture 44.

As is conventional in such containers, a portion 50 of one of the compartment walls (in this case, wall 14) is a septum capable of penetration by a cannula C, to allow whole blood to enter compartment 12, FIG. 3A. Wall 22 includes a passageway 46 capable of allowing liquid flow out of compartment 12 when not blocked by member 30. Walls 14 and 16 preferably include stop notches 52, 54 to releasably engage member 30 in its two operative positions, and an elastomeric seal ring 56 that extends the circumference of the walls 14, 16, 18 and 20, FIG. 2, to seal off air flow into compartment 18. The width of compartment 12 is the predetermined width "w" between walls 18 and 20. Compartment 12 can be square as shown, or rectangular. The longest dimension of compartment 12 is its length "L", FIG. 1.

In accordance with the invention, fixed maintaining means are provided that include porous mechanical means to resist flow of the heavier phase out of its compartment portion once centrifugal separation is achieved. As used herein, "mechanical means" refers to a structure that resists flow purely by physical action, as distinguished from chemical interaction due to charges or other chemical attraction. Preferably, such means comprise a collection of a plurality of surfaces. Any surfaces spaced a proper distance, and properly angled, can resist flow of the heavier phase out of portion A, FIG. 1, into portion B, simply by reason of the resistance created to outward flow by the close surfaces. Most preferably, such plurality of surfaces are in the form of baffle plates 60 fixedly mounted at 62, FIG. 1, preferably adjacent to the wall 24 against which the heavier of the two blood phases (the blood cells) is driven during centrifuging. Although wall 24 is shown as presenting a generally flat surface for such mounting, that is not critical and curved surfaces can also be used. Plates 60 are inclined at an angle beta defined as the angle subtended by the instantaneous slope of the plate as it diverges from the direction of the shear force F', arrow 72, FIG. 1, which operates tangential to the collection of plates 60. Preferably, this angle is a value that is between about 30° and about 120°, most preferably about 60°. Values less than or greater than this range tend to give insufficient resistance to shear. To insure that fluid attraction within the porous means is sufficient to resist shear forces, the distance between the plates (measured perpendicular to the plates, dimension "d", FIG. 1) is no larger than about 0.10 cm. For ease in manufacturing, and to avoid adversely affecting the blood cells, the smallest distance that is useful is about 0.018 cm. Most preferably, it is about 0.025 cm.

The thickness of the plates 60 is not critical. For example, they can be from about 0.01 cm to about 0.1 cm thick.

The length "l" of plates 60, FIG. 1, is that which insures that the plates extend out into the region where the blood serum is left just after centrifugation, FIG. 3C. The length can be longer than the value needed, but should not be shorter.

Any assembly technique can be used to form compartment 12. For example, plates 60 can be molded as part of first wall 24, FIG. 1, and then walls 14, 16, 18 and 20 are bonded to wall 24 and the edges of plate 60, such as at junction lines "J" using, e.g., solvent welding. The same assembly can be done at wall 22. As shown in FIG. 2, plates 60 preferably extend the full width "w" of compartment 12.

Prior to use, container 10 is assembled with member 30 shut against wall 22, FIG. 3A, and preferably a vacuum is drawn on the contents to form an evacuated container. When used, with or without an anticoagulant, whole blood enters the container through cannula C, and fills most of the container, FIG. 3B. At this point the container is spun in a centrifuge, FIG. 3C, so that centrifugal force F is applied. This causes the heavier blood cells (shown as circles) to push down between baffle plates 60, arrow 100, and the lighter blood serum ("s", shown dotted) to rise (arrow 102) and remain in the right-hand portion of compartment 12 (as shown). A phase separation line S is formed between the two phases, down inside the region between plates 60.

As soon as centrifugal force F ceases, gravity will pull the serum "s" down, generally creating a shear force F', FIG. 3D. Further shear occurs in the direction of force F' when member 30 is slid outward, arrow 112, to form a dispensing chamber 120 for the serum and to allow serum to transfer, arrow 118, to chamber 120. As is evident, member 30 also functions as the valve means to temporarily block liquid flow out through passageway 46 into such a chamber. As will be apparent, it is baffle plates 60 that resist and prevent remixing of the blood cells with the serum when shear force F' occurs. (A small amount of residual serum remains at S' at the ends of the baffle plates.)

Application of external pressure ΔP causes liquid to be dispensed at tip 42.

Alternatively, FIG. 4, plates 60A need not be planar as in FIG. 1, but can have a slight curve thereto, as long as the overall shape creates the desired angle beta. (For clarity only two of the many plates 60A actually used, are shown in container 10A.) Although a constant spacing is suggested for plates 60A, such is not necessary as the spacing can vary over the length 1 of the plates.

Alternatively, FIG. 5, plates 60B need not be anchored to wall 24B, but instead can be anchored to walls 18B and 20B (only 18B being shown), so as not to extend all the way to wall 24B.

Still another alternative to plates 60 is to use a porous filter media, not shown, of any convenient material, wherein the dimensional spacing between the strands or surfaces of the filter media is selected to be at least 20 mm, to avoid damaging the red cells. That is, the size must not impede or affect phase separation during centrifuging, and must not lyse the cells. However, most of the packing of the filter media should be such as to have maximum flow dimensions between the surfaces that do not exceed about 0.10 cm, for greatest resistance to an outflow of the separated heavier phase. When using such a filter media, the angle beta becomes less important, since the passages through the media may be randomly oriented, preventing a measurement of such angle.

Figure 6:
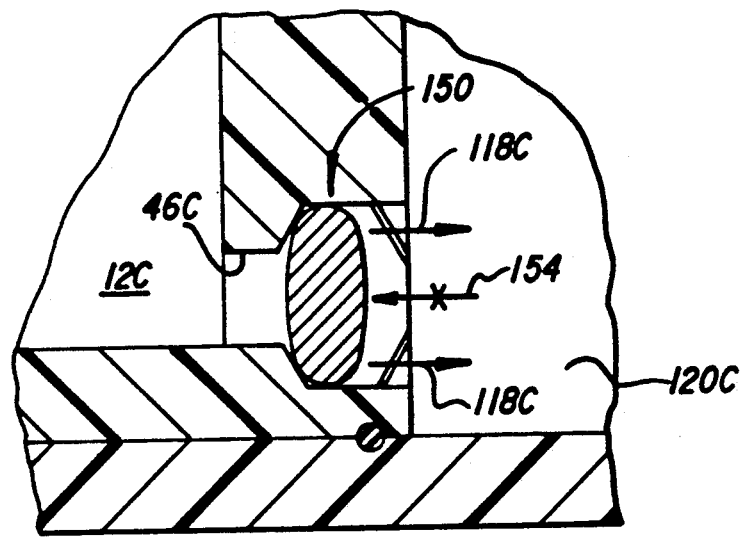
FIG. 6 is an enlarged, fragmentary elevational view in section showing an alternate embodiment of passageway 46.

Dispensing in such devices continues until passageway 46 is no longer covered by serum. Preferably, FIG. 6, passageway 46C includes a conventional one-way check-valve 150, which allows flow to occur from compartment 12C to chamber 120C, arrows 118C, but not in the reverse direction, arrow 154 with the "X". (Parts similar to those previously described use the same reference numeral, but with a "C" appended thereto.)

The invention has been described in detail with particular reference to preferred embodiments thereof, but it will be understood that variations and modifications can be effected within the spirit and scope of the invention.

What is claimed is:

1. In a centrifuge container for separating two phases of different specific gravities in a liquid by centrifuging the heavier phase away from the lighter phase, said container including a compartment for said liquid defined by opposing walls, and means in said compartment for maintaining said phases in separate regions of the compartment after centrifugation, the improvement wherein said means comprise fixed maintaining means that will accommodate expected variations in phase volumes, including porous mechanical means for resisting flow of the heavier phase out of its compartment portion in the presence of shear forces occurring when the lighter phase is drawn off, said mechanical means being disposed in said compartment region to be occupied by said heavier phase.

2. A container as defined in claim 1, wherein said mechanical means comprise a collection of a plurality of surfaces spaced close enough together to resist flow tangential to said collection, said surfaces being inclined at an angle to one of said walls.

3. In a centrifuge container for separating two phases of different specific gravities in a liquid by centrifuging the heavier phase away from the lighter phase, said container including a compartment for said liquid defined by opposing walls, and means in said compartment for maintaining said phases in separate regions of the compartment after centrifugation, the improvement wherein said means comprise fixed maintaining means that will accommodate expected variations in phase volumes, including a plurality of surfaces mounted on at least one of said opposing walls, said surfaces extending at an angle from the compartment region to be occupied by said heavier phase, towards the region of said compartment to be occupied by said lighter phase, said angle being selected to resist shear stress when the lighter phase is removed from the heavier phase, whereby the heavier phase is prevented from remixing with the lighter phase.

4. In a centrifuge container for separating two phases of different specific gravities in a liquid by centrifuging the heavier phase away from the lighter phase, said container including a compartment for said liquid defined by opposing walls, and means in said compartment for maintaining said phases separate after centrifugation, the improvement wherein said compartment includes a wall surface against which said heavier phase is to be pushed during centrifuging, and wherein said means comprise fixed maintaining means that will accommodate expected variations in phase volumes, including a plurality of surfaces mounted in said compartment adjacent said wall surface, said surfaces extending at an angle towards the region of said compartment to be occupied by said lighter phase, said angle being selected to resist shear stress when the lighter phase is removed from the heavier phase, whereby the heavier phase is prevented from remixing with the lighter phase.

5. A container as defined in claim 2, 3 or 4, wherein said angle is a value that is between about 30° and about 120° measured from the direction of the shear force created when the lighter phase is removed.

6. A container as defined in claim 2, 3 or 4, wherein said compartment has a predetermined width and said means comprise a plurality of baffle plates each extending the full width of said compartment.

7. A container as defined in claim 6, wherein the distance between said plates is from about 0.018 cm to about 0.1 cm.

8. A container as defined in claim 2, 3 or 4, and further including means forming a serum dispensing chamber, a passageway connecting said chamber and said compartment, and means for temporarily blocking liquid flow to said chamber from said compartment.

9. A container as defined in claim 8, and further including one-way valve means for allowing flow of liquid through said passageway only from said compartment to said chamber.

* * * * *